(12) United States Patent
Hasegawa

(10) Patent No.: US 10,987,180 B2
(45) Date of Patent: Apr. 27, 2021

(54) FLEXIBLE MANIPULATOR

(71) Applicant: Olympus Corporation, Hachioji (JP)

(72) Inventor: Mitsuaki Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 293 days.

(21) Appl. No.: 16/171,430

(22) Filed: Oct. 26, 2018

(65) Prior Publication Data

US 2019/0060016 A1 Feb. 28, 2019

Related U.S. Application Data

(63) Continuation of application No. PCT/JP2016/086054, filed on Dec. 5, 2016.

(51) Int. Cl.
*A61B 34/00* (2016.01)
*A61B 90/90* (2016.01)
(Continued)

(52) U.S. Cl.
CPC .............. *A61B 34/71* (2016.02); *A61B 90/90* (2016.02); *B25J 18/06* (2013.01); *A61B 17/29* (2013.01);
(Continued)

(58) Field of Classification Search
CPC ............ A61B 34/71; A61B 2034/2061; A61B 2034/715; A61B 17/29; A61B 2090/061; A61M 25/0147
See application file for complete search history.

(56) References Cited

U.S. PATENT DOCUMENTS 5,174,168 A 12/1992 Takagi et al.
9,259,277 B2 2/2016 Rogers et al.
(Continued)

FOREIGN PATENT DOCUMENTS

EP 3 112 097 A1 1/2017
EP 3 143 921 A1 3/2017
(Continued)

OTHER PUBLICATIONS

International Search Report from corresponding Japanese Application No. PCT/JP2016/086054, dated Feb. 21, 2017.
(Continued)

*Primary Examiner* — Robert A Lynch
(74) *Attorney, Agent, or Firm* — Scully, Scott, Murphy & Presser, P.C.

(57) ABSTRACT

The technology disclosed herein is directed to a flexible manipulator used to prevent a loss of control of a movable part by reducing the friction applied to the power transmission member and to be able to suppress the occurrence of a path length difference of a plurality of power transmission members with regard to various curvature length of an insertion part. The flexible manipulator includes an elongated member formed in the shape of a long flexible tube and having two or more paths that pass through in a longitudinal direction on the outside in the radial direction with regard to a center axis. Respective movable and driving parts is disposed on respective tip and base ends of the elongated member. Power transmission members are arranged to pass through the path of the elongated member and that transfer the power of the driving part to the movable part.

13 Claims, 8 Drawing Sheets

(51) Int. Cl.
  *B25J 18/06*   (2006.01)
  *A61B 17/00*   (2006.01)
  *A61B 17/29*   (2006.01)
  *A61B 90/00*   (2016.01)
  *A61M 25/01*   (2006.01)
  *A61B 34/20*   (2016.01)

(52) U.S. Cl.
  CPC ............... *A61B 2017/00017* (2013.01); *A61B 2017/0034* (2013.01); *A61B 2017/00327* (2013.01); *A61B 2017/00398* (2013.01); *A61B 2017/2903* (2013.01); *A61B 2017/2905* (2013.01); *A61B 2034/2061* (2016.02); *A61B 2034/715* (2016.02); *A61B 2090/061* (2016.02); *A61M 25/0147* (2013.01)

(56) References Cited

U.S. PATENT DOCUMENTS

| | | |
|---|---|---|
| 2005/0174168 A1 | 8/2005 | Hirotsugu et al. |
| 2009/0259277 A1 | 10/2009 | Cornejo Cruz et al. |
| 2016/0135662 A1 | 5/2016 | Hatakeyama et al. |
| 2016/0136810 A1 | 5/2016 | Wakai et al. |
| 2016/0166341 A1* | 6/2016 | Iordachita ............ A61B 34/35 606/130 |
| 2016/0166347 A1 | 6/2016 | Kishi |
| 2016/0287346 A1 | 10/2016 | Hyodo et al. |
| 2016/0345801 A1 | 12/2016 | Kishi |
| 2017/0049523 A1 | 2/2017 | Yoshi |
| 2017/0080581 A1 | 3/2017 | Iida et al. |
| 2017/0209227 A1 | 7/2017 | Yoshimura |
| 2019/0117325 A1 | 4/2019 | Kishi |

FOREIGN PATENT DOCUMENTS

| | | |
|---|---|---|
| JP | 64-071686 | 3/1989 |
| JP | 2002-200091 | 7/2002 |
| JP | 2015-024033 | 2/2015 |
| JP | 2015-042234 | 3/2015 |
| JP | 2015-156944 A | 9/2015 |
| JP | 2015-217016 A | 12/2015 |
| JP | 2016-002414 | 1/2016 |
| WO | 2015-012242 | 1/2015 |
| WO | 2015-093602 | 6/2015 |
| WO | 2016-136301 | 9/2016 |

OTHER PUBLICATIONS

Japanese Office Action dated Mar. 10, 2020 in Japanese Patent Application No. 2018-555335.
International Search Report and Written Opinion from corresponding International Application No. PCT/JP2016/086054, dated Mar. 7, 2017.

* cited by examiner

FLEXIBLE MANIPULATOR

CROSS-REFERENCE TO RELATED APPLICATION

This application is a continuation application of PCT Application No. PCT/JP2016/086054 filed on Dec. 5, 2016, which is hereby incorporated by reference in its entirety.

TECHNICAL FIELD

The disclosed technology relates generally to manipulators and more particularly, to a flexible manipulator used in medical technology.

DESCRIPTION OF THE RELATED ART

In general, two lumens are formed for respectively guiding two wires so as to drive a movable portion straight along a longitudinal direction of a flexible insertion portion inside the insertion portion. However, when the insertion portion is curved, a difference occurs in the path length of the two wires, and one wire is stretched while the other is loosened, and therefore the movable portion will move in an unintended direction. To overcome this problem, Patent Application WO 2015/093602 discloses a flexible manipulator having a plurality of lumens spirally twisted around a longitudinal axis of the insertion portion.

In accordance to Patent Application WO 2015/093602, the difference in the path length can be reduced, and the movable portion moving in an unintended direction can be suppressed by maintaining the twisting pitch of the spiral lumens to be within a predetermined range.

BRIEF SUMMARY OF EMBODIMENTS

In light of the foregoing, embodiments of the technology disclosed herein are directed to a flexible manipulator. The flexible manipulator includes an elongated portion, a movable potion, a driving portion, two or more long narrow power transmission portions, a curvature length measuring portion, and a curvature length adjusting portion. The elongated portion is formed as a long narrow flexible tube with two or more paths that pass through in a longitudinal direction on an outside in a radial direction with regard to a center axis thereof. The movable potion is located on a tip end of the elongated portion. The driving portion is located on a base end of the elongated portion. The two or more long narrow power transmission portions is configured to pass through the path of the elongated portion so as to transmit the power of the driving portion to the movable portion. The curvature length measuring portion is configured to measure a curvature length of the elongated portion. The curvature length adjusting portion is configured to cause bending in the vicinity of the base end of the elongated portion so as to adjust the curvature length of the elongated portion as a predetermined length.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
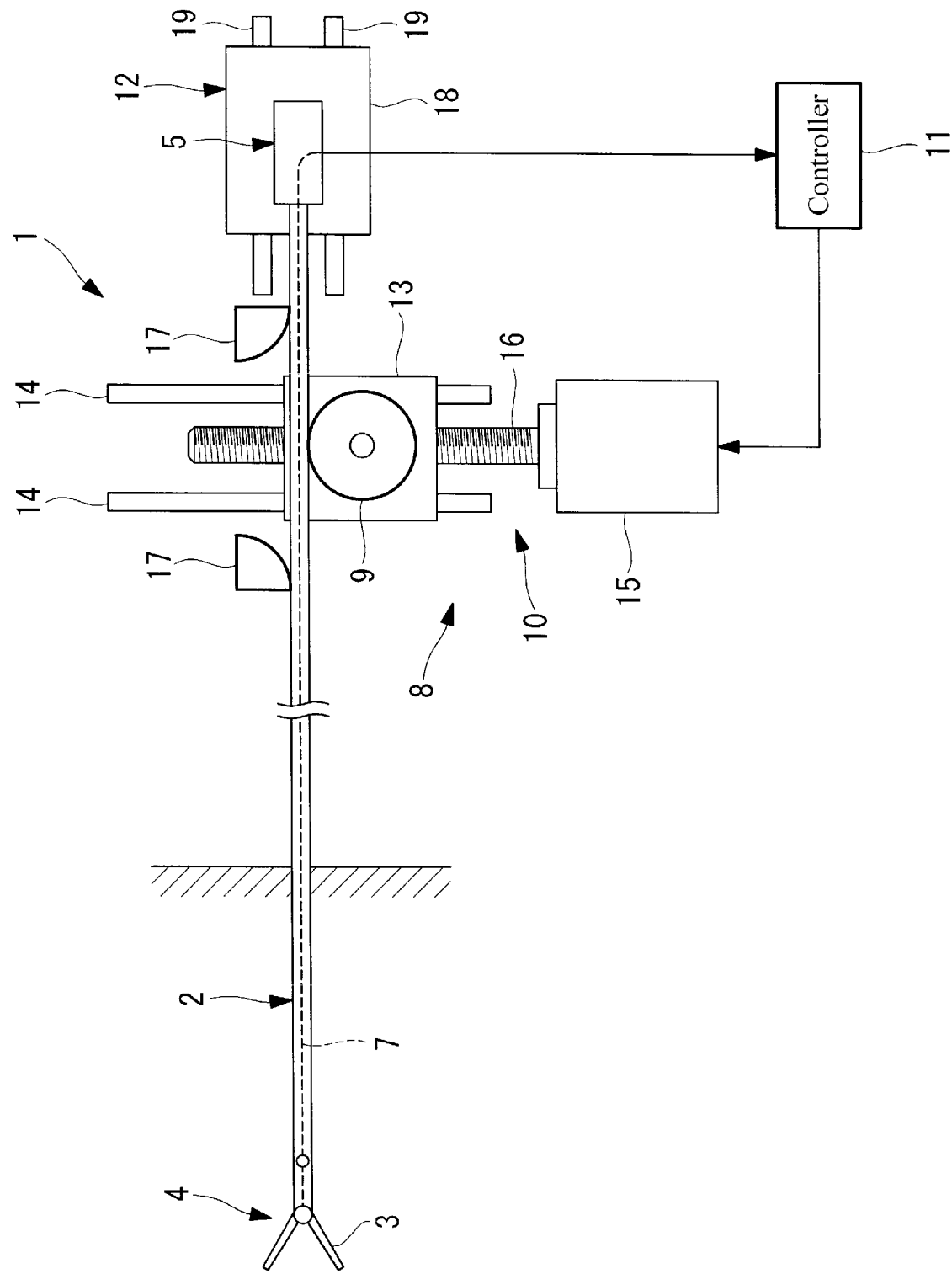
FIG. 1 is schematic diagram illustrating a flexible manipulator according to the first embodiment of the technology disclosed herein.

The technology disclosed herein is directed to a flexible manipulator used to prevent a loss of control of a movable portion by reducing the friction applied to the power transmission portion and to be able to suppress the occurrence of a path length difference of a plurality of power transmission portions with regard to various curvature length of an insertion portion. The flexible manipulator includes an elongated portion formed in the shape of a long flexible tube and having two or more paths that pass through in a longitudinal direction on the outside in the radial direction with regard to a center axis. A movable portion is disposed on a tip end of the elongated portion and a driving portion is disposed at a base end of the elongated portion. Two or more long narrow power transmission portions are arranged to pass through the path of the elongated portion and that transfer the power of the driving portion to the movable portion. A curvature length measuring portion that measures the curvature length of the elongated portion and a curvature length adjusting portion that causes curvature in the vicinity of the base end of the elongated portion such that the curvature length of the elongated portion is a predetermined length. Various embodiments for the flexible manipulator are described in detail hereinafter which suppresses the occurrence of path length difference of a plurality of power transmission portions, with regard to various curvature lengths of the insertion portion, and prevents a loss of control of the movable portion by reducing the friction applied to the power transmission portion.

It should be noted that the curvature length of an insertion portion of a flexible manipulator changes based on the insertion path, and therefore when attempting to resolve the aforementioned problem by using a spiral lumen with a predetermined twisting pitch with regard to various curvature length, there is a need to twist the lumen with a sufficiently short pitch. However, when the twisting pitch is shortened, the friction with the wire that is provided inside will increase, and there is a problem that the control properties of the movable portion are reduced.

In light of the foregoing, embodiments of the technology disclosed herein are directed to a flexible manipulator that (i) suppresses the occurrence of path length difference of a plurality of power transmission portions, with regard to various curvature lengths of the insertion portion, and (ii) prevents a loss of control of the movable portion by reducing the friction applied to the power transmission portion.

One embodiment of the technology disclosed herein is a flexible manipulator including an elongated portion formed in the shape of a long flexible tube and having two or more paths that pass through in a longitudinal direction on the outside in the radial direction with regard to a center axis of the elongated portion. A movable portion is disposed on a tip end of the elongated portion and a driving portion disposed at a base end of the elongated portion. Two or more long narrow power transmission portions are arranged to pass through the path of the elongated portion and that transfer the power of the driving portion to the movable portion. A curvature length measuring portion measures the curvature length of the elongated portion and a curvature length adjusting portion causes curvature in the vicinity of the base end of the elongated portion such that the curvature length of the elongated portion is a predetermined length.

According to this embodiment, when the driving portion is operated, the generated power is transmitted to the movable portion by the power transmission portion that passes through the inside of the path formed, and the movable portion is operated. When the long narrow flexible insertion portion is curved, the shape of the path in the elongated portion through which the power transmission portion passes is changed in conjunction with the curvature.

The curvature shape of the insertion portion is determined by the shape or the like of insertion partner, or in other words the body cavity to the target organ in the body of the patient, and therefore the curvature length is not fixed. In this regard, the curvature length of the elongated portion is measured by the curvature length measuring portion, and the vicinity of the base end of the elongated portion is curved by the curvature length adjusting portion, and hence the curvature length adjusting portion is adjusted to a predetermined curvature length that eliminates the path length difference. For example, when the path extends straight along the longitudinal direction of the elongated portion, the path length difference generated by the elongated portion curving in one direction can be eliminated by causing other parts of the elongated portion to curve by the same curvature length in the opposite direction. Furthermore, for example, when the path extends in a spiral with a predetermined pitch along the center axis of the elongated portion, the path length difference generated by the elongated portion curving in one direction is eliminated by causing other parts of the elongated portion to curve such that the total curvature length is an integer multiple of the pitch.

With the present embodiment, a curvature length adjusting portion is provided in the vicinity of the base end of the elongated portion, and therefore even when the tip end of the elongated portion is inserted in the body, adjustment is possible in the vicinity of the base end outside the body so that the path length difference is eliminated. The occurrence of path length difference of the plurality of the power transmission portion is suppressed with regard to the various curvature lengths of the elongated portion, and a loss of control of the movable portion is prevented by reducing the friction applied to the power transmission portion.

In the aforementioned embodiment, the path is formed in a spiral shape around the center axis, and the predetermined length can be an integer multiple of the pitch of the path.

With this configuration, the curvature length can easily be adjusted so that the total curvature length is an integer multiple of the pitch of the spiral path. When the spiral path pitch formed in the elongated portion is fixed, the occurrence of a path length difference of the plurality of power transmission portions is suppressed, and a loss of control of the movable portion is prevented by reducing the friction applied to the power transmission portion. Furthermore, the predetermined length is the length that minimizes the difference to the curvature length measured by the curvature length measuring portion. Therefore, the amount of adjusting of the curvature length is minimized, and a loss of control of the movable portion is prevented by suppressing the increase in the friction applied to the power transmission portion. The curvature length adjusting portion may have a pressing portion made to contact the elongated portion from the outside in the radial direction in the vicinity of the base end of the elongated portion, and a pressing portion driving mechanism that causes the pressing portion to move in the radial direction of the elongated portion. Thus, the elongated portion can easily be curved and the path length difference can be eliminated by the pressing of the pressing portion inward in the radial direction from the outside in the radial direction of the elongated portion, by operating the pressing portion driving mechanism.

In addition, a linear moving mechanism may be provided that causes the driving portion to move in the direction of the longitudinal axis of the elongated portion, synchronous to the movement of the pressing portion by the pressing portion driving mechanism. And thereby, movement in the direction of the longitudinal axis of the elongated portion caused by increasing the curvature length of the elongated portion can be compensated by causing movement of the driving portion by the linear moving mechanism. It is not necessary to move the movable portion in the longitudinal direction of the elongated portion.

In the aforementioned embodiment, the pressing portion may have a cylindrical outer peripheral surface with a predetermined radius provided such that the elongated portion extends along the circumferential direction. The radius of the curvature of the elongated portion that is curved by being pressed by the pressing portion is equal to or larger than the radius of the cylindrical outer peripheral surface, and thus sudden curvature can be prevented. The pressing portion can be a pulley or the likes. Thus, a pressing portion with a cylindrical outer peripheral surface of a predetermined radius can easily be constructed by a pulley, and the friction between the elongated portion and the pressing portion that is pressed on the elongated portion can be released by the rotation of the pulley.

Figure 2:
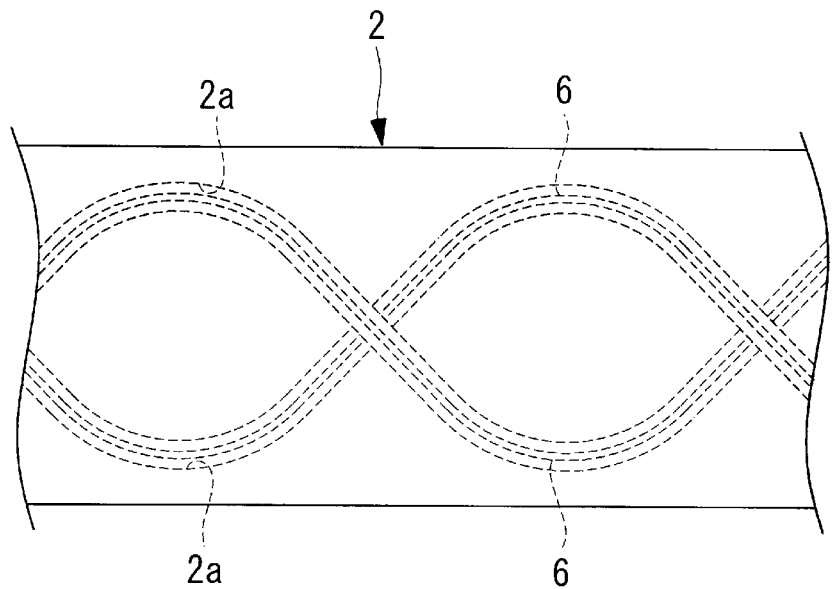
FIG. 2 is a side surface diagram illustrating an insertion portion of the flexible manipulator of FIG. 1.

As illustrated in FIG. 1 and FIG. 2, the flexible manipulator 1 according to the present embodiment includes an insertion portion or elongated portion 2 having a plurality of inner holes or paths 2a that is inserted into a body cavity of a patient via a forceps channel of an endoscope. Respective opposed ends of the flexible manipulator 1 includes a movable portion 4 and a driving portion 5, respectively. The movable portion 4 with a treatment portion 3 such as a joint and grasping forceps and the like is located on the tip end of the insertion portion or elongated portion 2. The driving portion 5 that operates the movable portion 4 is located on the base end of the insertion portion or elongated portion 2. A wire or power transmission portion 6 passes through the inner holes 2a in a longitudinal direction and transmits the power generated by the driving portion 5 to the movable portion 4. Curvature length measuring portion 7 measures the total curvature length (curvature length) of the insertion portion or elongated portion 2, and curvature length adjusting portion 8 that adjusts the total curvature length of the insertion portion 2.

The insertion portion or elongated portion 2 is formed in a flexible tube shape that is curved across the entire length or a portion thereof in the longitudinal direction. The driving portion 5 includes an electric motor (not shown), and is configured so as to tow the wire or power transmission portion 6 toward the base end side. In the example illustrated in FIG. 2, the inner hole 2a located in the insertion portion 2 passes through the insertion portion 2 in the longitudinal direction at a position shifted to the outside in the radial direction from the center axis of the insertion portion 2 by being configured in a spiral at a predetermined pitch. The tension of one wire or power transmission portion 6 is increased by the power of the electric motor of the driving portion 5 and the tension of the wire or power transmission portion 6 on the other side is decreased, so the tension difference between the two wires or power transmission portions 6 is transferred to the movable portion 4 located on the tip end of the insertion portion or elongated portion 2 as power, and thus the joint of the movable portion 4 can swing.

The curvature length measuring portion 7 that hereinafter is also referred to as an optical fiber sensor 7 can measure the total curvature length of the insertion portion or elongated portion 2. The optical fiber sensor 7 is provided across the entire length along the longitudinal direction of the insertion portion 2 and is curved to the same curvature length along the curvature of the insertion portion 2. The total curvature length provided by the insertion portion 2 can be measured by the difference between the light incoming from the base end side of the optical fiber sensor 7 and the detected light that returns to the base end side of the optic fiber sensor 7. The curvature length adjusting portion 8 includes a pressing portion 9 located in the vicinity of the base end of the insertion portion 2, which causes contact from the outside in the radial direction onto the outer surface of the insertion portion 2. A pressing portion driving mechanism 10 that moves the pressing portion 9 in a direction that presses the insertion portion 2. A control portion 11 that controls the pressing portion driving mechanism 10, and a linear moving mechanism 12 that causes movement of the driving portion 5 in the direction of the longitudinal axis of the insertion portion 2, and synchronizes to the movement of the pressing portion 9 by the pressing portion driving mechanism 10.

The pressing portion 9 that hereinafter is also referred to as a pulley 9 rotatably positioned around the axis line that intersects with a surface that includes the longitudinal axis of the insertion portion 2, and having a cylindrical outer peripheral surface with predetermined outer radial dimensions. The outer radial dimensions of the outer peripheral surface of the pulley 9 is largely set by the minimum curvature radius of the insertion portion 2 where the optic fiber sensor 7 is inserted.

The pressing portion driving mechanism 10 includes a slider 13 supported to be linearly movable in the direction along the flat surface that rotatably supports the pulley 9, a guide rail 14 that guides the straight-line movement of the slider 13, and an electric motor 15 and ball screw 16 that drives the slider 13. When the electric motor 15 and the ball screw 16 are operated to linearly move the slider 13 in one direction, the insertion portion 2 is radially pressed by the outer peripheral surface of the pulley 9 mounted on the slider 13, and the insertion portion 2 is curved along the circumferential direction on the outer peripheral surface of the pulley 9.

A guide portion 17 with an arcuate guide surface having outer radial dimensions essentially equal to the pulley 9 is positioned on the side opposite to the pulley 9 with the insertion portion 2 interposed therebetween at an interval on both sides, sandwiching the movable range of the slider 13. When the insertion portion 2 is curved in one direction by the pulley 9, a curved portion is formed in an opposite direction on both sides of the curvature due to the pulley 9, and therefore these parts cannot be curved at a radius smaller than the minimum curvature radius of the insertion portion 2, so as to guide the curvature by the guide surface of the guide portion 17.

The linear moving mechanism 12 has a slider 18 on which the driving portion 5 is mounted, and a guide rail 19 that supports the slider 18 in a manner that can linearly move in the longitudinal direction of the insertion portion 2.

Figure 3:
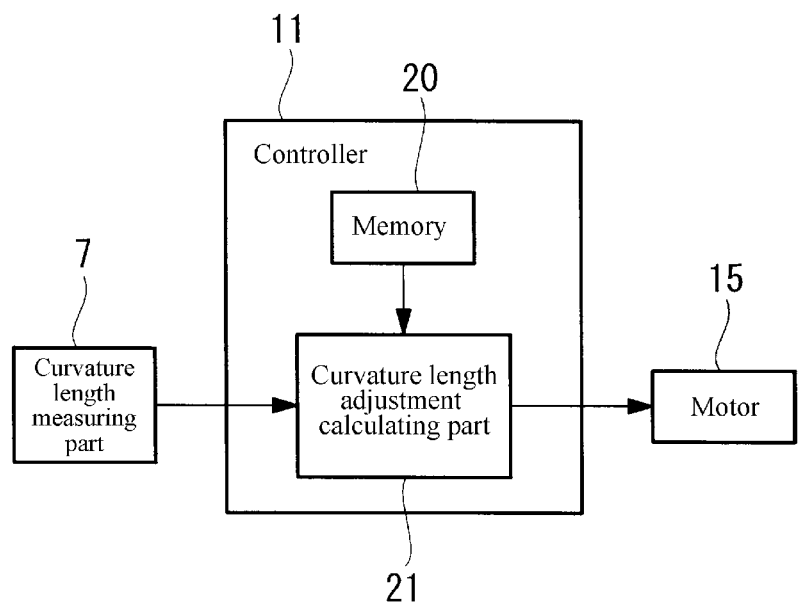
FIG. 3 is a block diagram for describing the control portion of the flexible manipulator of FIG. 1.

A controller 11 controls the electric motor 15 of the pressing portion driving mechanism 10 so that the total curvature length of the insertion portion 2 measured by the optical fiber sensor 7 is an integer multiple of the pitch of the inner hole 2a in the insertion portion 2. As illustrated in FIG. 3, the controller 11 includes a memory 20 for storing the pitch of the inner holes 2a in the insertion portion 2, and the curvature length adjustment amount calculating portion 21 for calculating the amount of movement of the pulley 9 by the pressing portion driving mechanism 10 based on the total curvature length measured by the optical fiber sensor 7 and the pitch read from the memory 20.

The operation of the flexible manipulator 1 according to an embodiment configured in this manner is described below. In order to treat a part of a patient's body using the flexible manipulator 1 according to the present embodiment, the insertion portion 2 is inserted into the body of the patient from the movable portion 4 side, and is placed in a condition where the base end side is exposed outside of the patient's body. Then, the insertion portion 2 is curved to match the shape of the body cavity of the patient, and the movable portion 4 of the tip end is placed at a position suitable for treating the affected part. In this condition, the detection light is provided to the optic fiber sensor 7 which is the curvature length measuring portion, and the total curvature length $L_0$ of the insertion portion 2 is measured by detecting the light that returns at the tip end.

Furthermore, the curvature length adjustment amount calculating portion 21 in the controller 11 calculates the amount of movement "S" of the pulley 9 based on the pitch "P" of the inner holes 2a that is stored in the memory 20, and the total curvature length $L_0$ of the insertion portion 2 measured by the curvature length measuring portion 7, and a command signal corresponding to the amount of movement S is output to the electric motor 15 of the pressing portion driving mechanism 10. In other words, the movement amount "S" of the pulley 9 is calculated based on the following formula by adding the curvature length ΔL that was newly generated by the insertion portion 2 being pressed in the radial direction by the moved pulley 9 to the total curvature length $L_0$ that was measured by the optical fiber sensor 7, and the new total curvature length (predetermined length) $L_1$ that is calculated will be a integer multiple of the pitch "P".

$$L1 = L0 + \Delta L = kP$$

$$S = f(\Delta L)$$

Herein, f(ΔL) is a function of ΔL, and k is a positive integer.

The newly generated curvature length ΔL includes both a portion that curves along the outer peripheral surface of the pulley 9, and a portion that curves along the guiding surface of the guiding portion 17. Herein, the movement amount "S" of the pulley 9 is stored in the curvature length adjustment amount calculating portion 21 as a function f(ΔL) of the new curvature length ΔL, but the movement amount "S" of the pulley 9 and the curvature length ΔL may be stored in association with each other.

Furthermore, in the present embodiment, the newly generated curvature length ΔL is preferably set to be as small as possible. Therefore, excess increase in the total curvature length is prevented, and excessive increase in the friction between the wire 6 and the inner wall of the inner hole 2a is suppressed.

Figure 4:
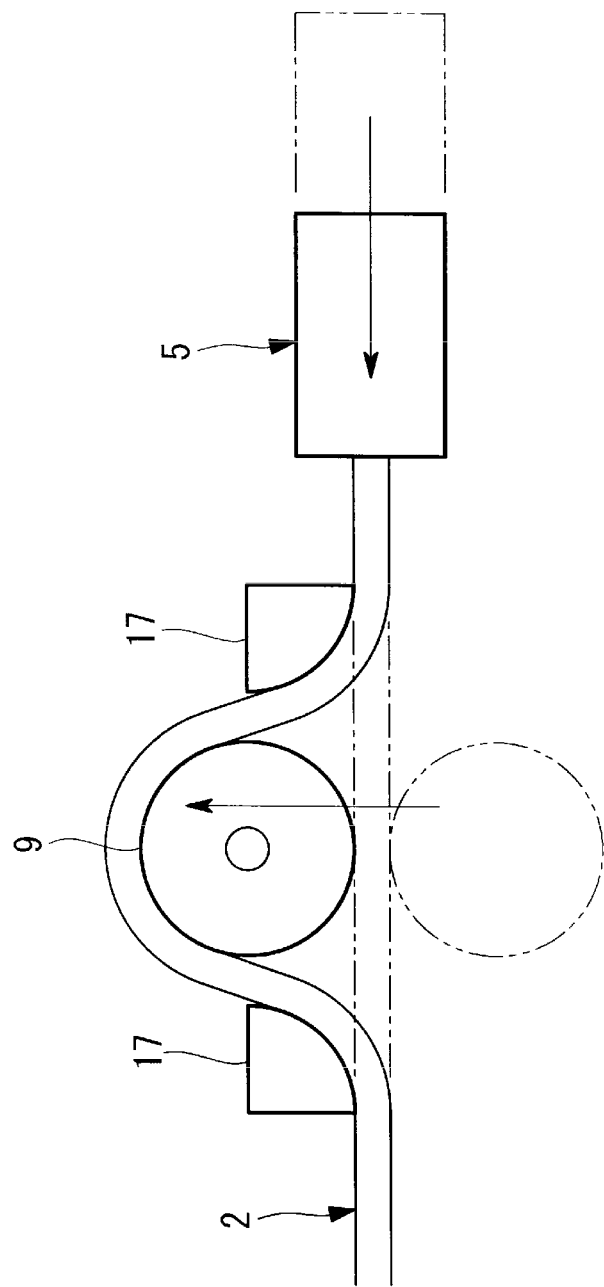
FIG. 4 is a schematic diagram for describing the adjustment operation of the curvature length by the flexible manipulator of FIG. 1.

As illustrated in FIG. 4, the slider 13 is linearly moved by driving the electric motor 15 and the pulley 9 is pressed to the outer surface of the insertion portion 2. When the insertion portion 2 is curved, tension will be generated in the insertion portion 2 and the driving portion 5 will be drawn to the tip end side, but the driving portion 5 is movably supported in the longitudinal direction of the insertion portion 2, so the slider 18 is linearly moved along the guide rail 19, which therefore excess tension is avoided from acting on the insertion portion 2. When the new curvature length is curved by ΔL by being pressed by the pulley 9, the total curvature length detected by the optic fiber sensor 7 is an integer multiple of the pitch of the inner hole 2a. Therefore, the path length difference of the inner hole 2a is relieved, and the occurrence of a tension difference caused by the curvature of the insertion portion 2 that occurs in the power transmission portions or wires 6 is prevented. Therefore, with the flexible manipulator 1 according to the present embodiment, the occurrence of a path length difference due to the curvature of the insertion portion 2 is prevented, so there is an advantage that the movable portion 4 can be prevented from moving in an unexpected direction. In particular, the present embodiment has an advantage that the path length difference of the inner hole 2a can easily be resolved simply by curving in the vicinity of the base end of the insertion portion 2 that is exposed outside of the patient's body.

Figure 5:
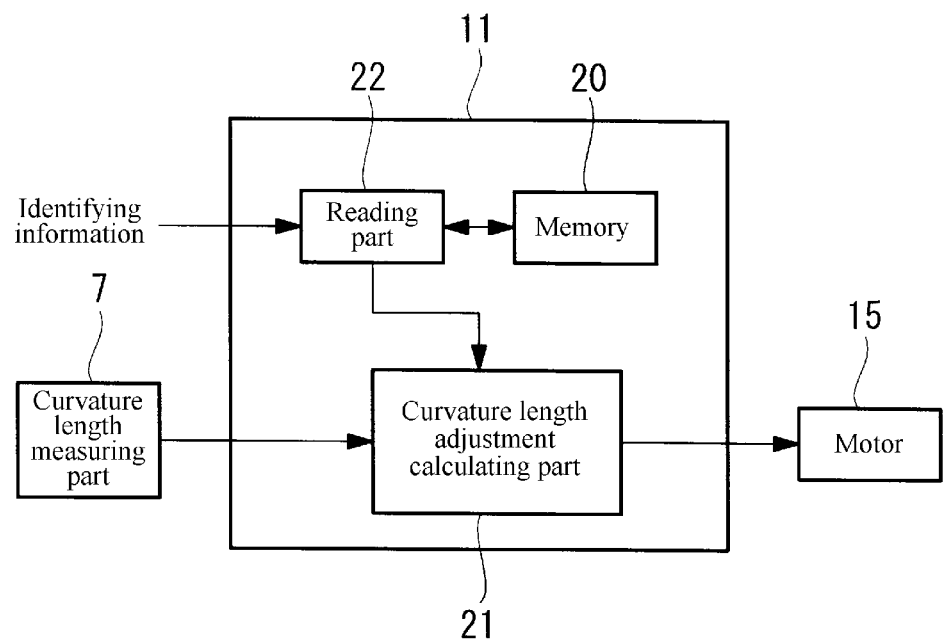
FIG. 5 is a block diagram illustrating an alternate example of FIG. 3.
Figure 6:
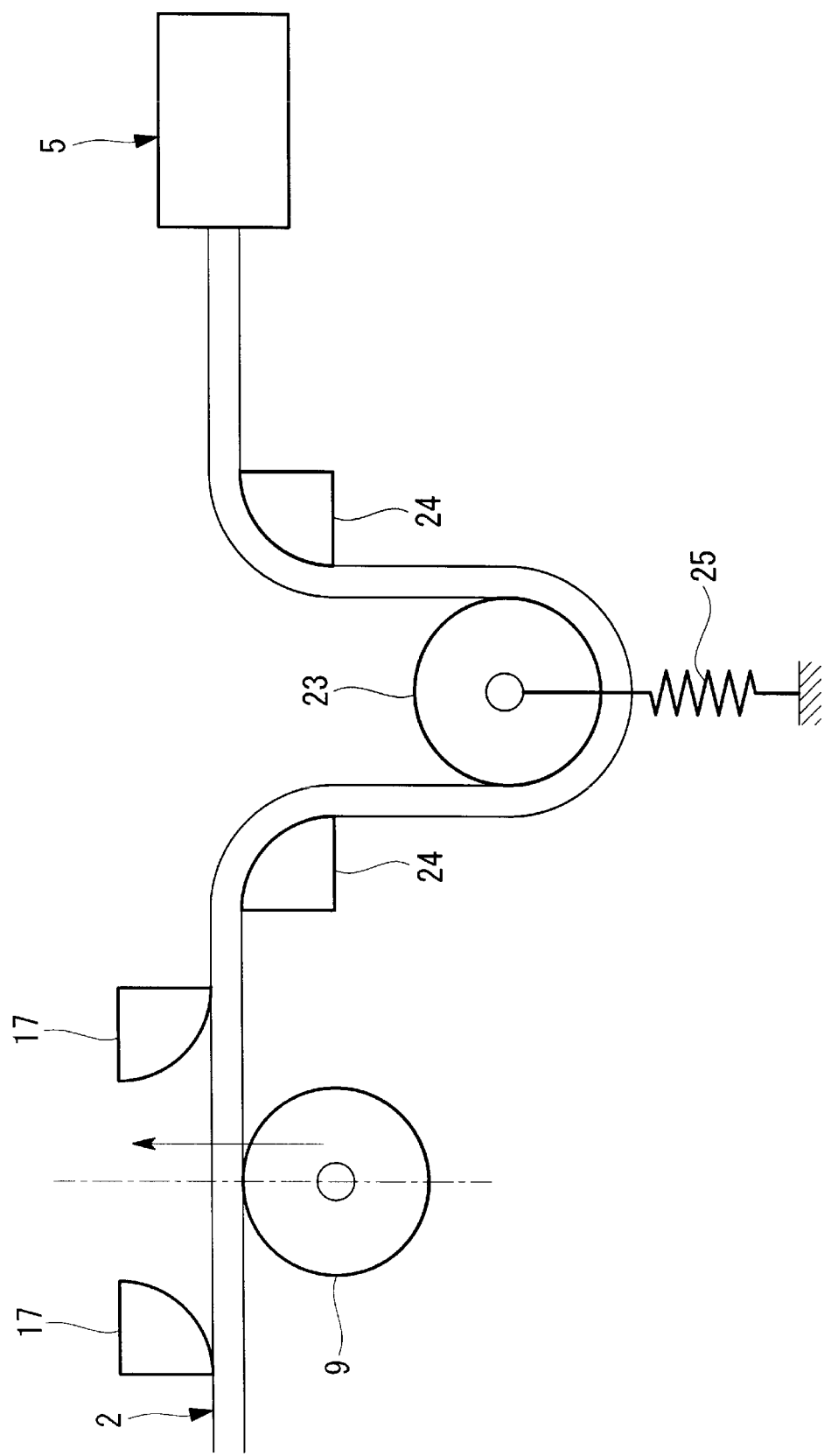
FIG. 6 is a schematic diagram illustrating an alternate example of FIG. 4.
Figure 7:
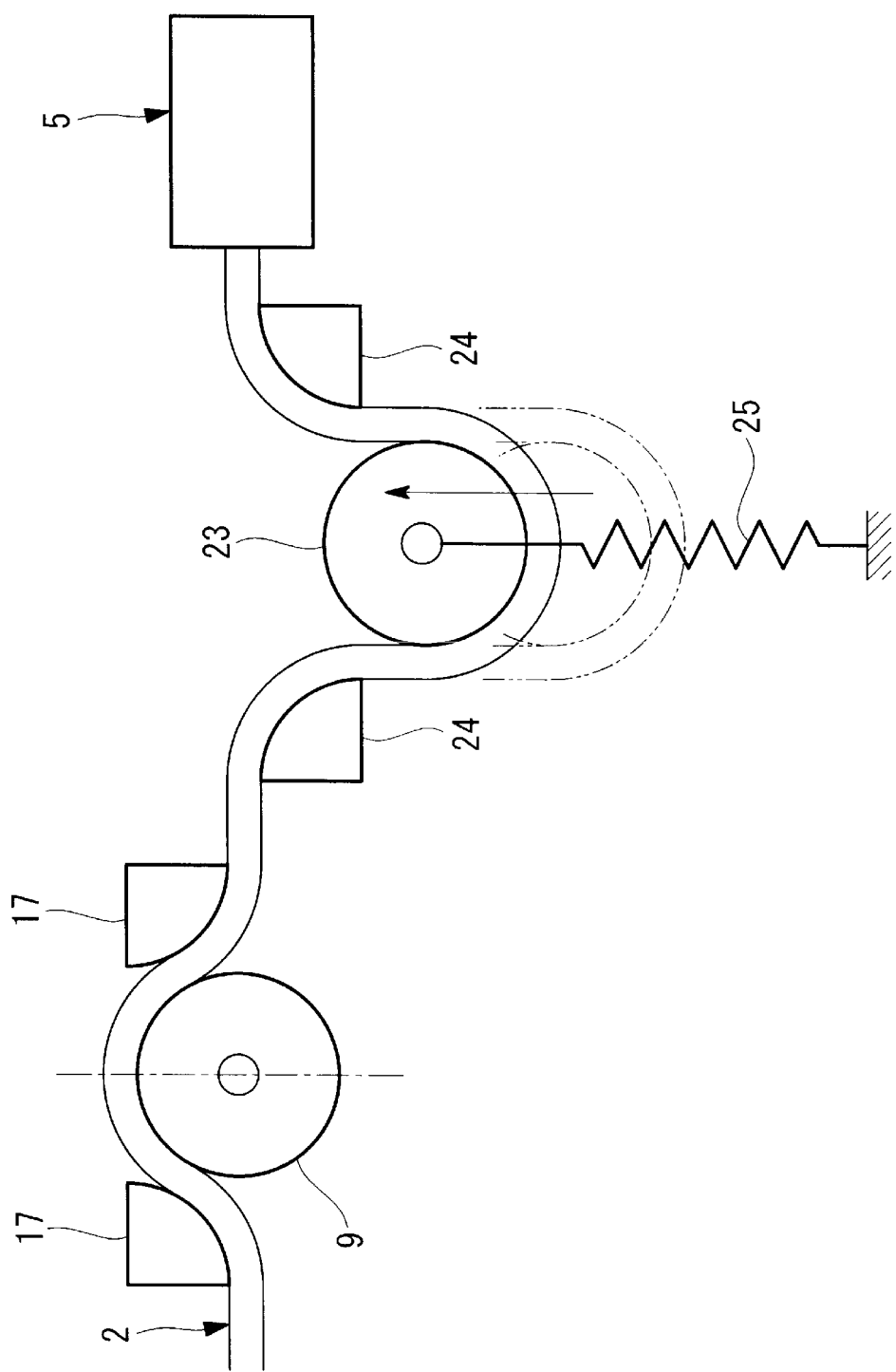
FIG. 7 is a schematic diagram for describing the operation of FIG. 6.

Incidentally, with the present embodiment, if the insertion portion 2 changes to another insertion portion 2 with a different pitch for the inner hole 2a, a storage portion not illustrated in the drawings that stores the identifying information for each insertion portion 2 is provided, and a reading portion 22 that reads the identifying information is provided in the controller 11 as illustrated in FIG. 5. In this case, the pitch of the inner hole 2a and the identifying information of the insertion portion 2 is stored in relation to each other in the memory 20. Therefore, if the insertion portion 2 is replaced, the pitch of the inner hole 2a is automatically read without being newly set, and thus the path length difference is eliminated. Furthermore, in the aforementioned embodiment, the driving portion 5 is mounted on the slider 18, and is movably supported in the longitudinal direction of the insertion portion 2 along the guide rail 19, but instead, a movable pulley 23 and a guiding portion 24 and an elastic portion 25 that biases the movable pulley 23 can be provided in the vicinity of the base end of the insertion portion 2, as illustrated in FIGS. 6 and 7. The movable pulley 23 is positioned in a manner that can move in the radial direction of the insertion portion 2. Moreover, the elastic portion 25 is biased in the direction where the movable pulley 23 is moved away from the guiding portion 24.

By wrapping the insertion portion 2 in a curved condition on the movable pulley 23 and the guide portion 24, and providing a portion where the insertion portion 2 linearly extends between the movable pulley 23 and the guide portion 24, the curvature length is prevented from changing simply by changing the length of the linear portion, even if the movable pulley 23 moves, as illustrated in FIG. 7. When the pressing portion driving mechanism 10 drives the pulley 9 to curve the insertion portion 2, the tension generated in the insertion portion 2 moves the movable pulley 23 against the biasing force of the elastic portion 25, and as a result, excess tension is prevented from acting on the insertion portion 2 while the driving portion 5 is fixed in place.

Figure 8:
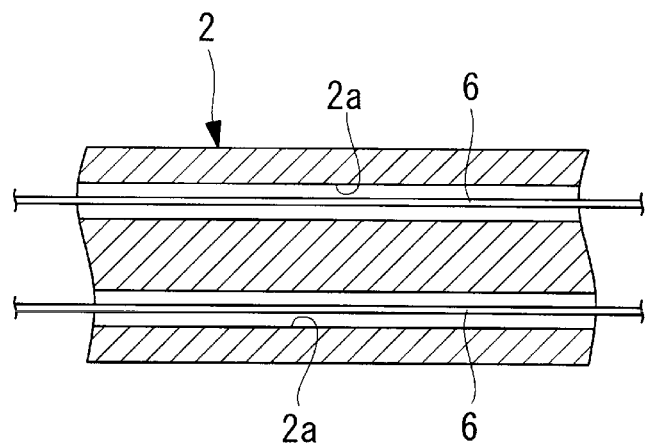
FIG. 8 is a longitudinal cross-section diagram illustrating an alternate example of FIG. 2.
Figure 9:
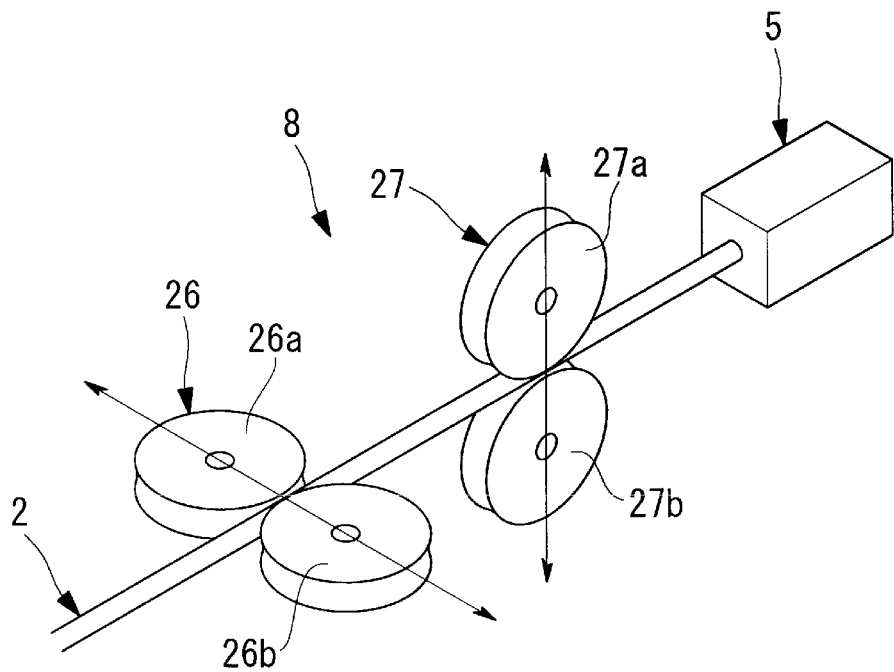
FIG. 9 is a schematic diagram illustrating an alternate example of FIG. 4.

In the present embodiment, the case where the inner hole 2a of the insertion portion 2 was formed in a spiral shape with a predetermined pitch was described, but instead, a case with an inner hole 2a that extends linearly along the longitudinal direction of the insertion portion 2 can be applied, as illustrated in FIG. 8. In this case, as illustrated in FIG. 9, two or more pulley sets 26, 27 that caused the insertion portion 2 to curve in different directions are located at different positions in the longitudinal direction of the insertion portion 2, as curvature length adjusting portion 8.

Each pulley set 26, 27 has two respective pulleys 26a, 26b, 27a, 27b supported on a slider (not illustrated in the drawings) so as to be rotatable around substantially parallel axis, and the insertion portion 2 is sandwiched in the radial direction between the outer peripheral surfaces of both respective pulleys 26a, 26b, 27a, 27b. By changing the direction that the insertion portion 2 is sandwiched by the pulley sets 26, 27 and making the moving planes of the sliders that support the pulley sets 26, 27 to differ as indicated by the arrows in FIG. 9, curvature in different directions is possible at different positions in the longitudinal direction of the insertion portion 2. In this case, the optical fiber sensor 7 which is the curvature length measuring portion is preferably able to detect the curvature length of the insertion portion 2 in association with the three-dimensional curvature direction. Moreover, if the inner hole 2a is linear, the optical fiber sensor 7 preferably detects curvature in one direction of the insertion portion 2 as a positive value, and detects the curvature in the opposite direction as a negative value. The path length difference of the inner hole 2a in this case is canceled by the insertion portion 2 being curved by the same length in the opposite direction (S-shaped), and therefore the curvature in the opposite direction is detected with a different sign by the optical fiber sensor 7. Furthermore, by sandwiching the insertion portion 2 by the two respective pulleys 26a, 26b, 27a, 27b, the curvature direction of the insertion portion 2 is changed to the opposite direction by moving the pulley sets 26, 27 to one pulley 26a, 27a side or moving the pulley sets 26, 27 to the other side of the pulley 26b, 27b.

Figure 10:
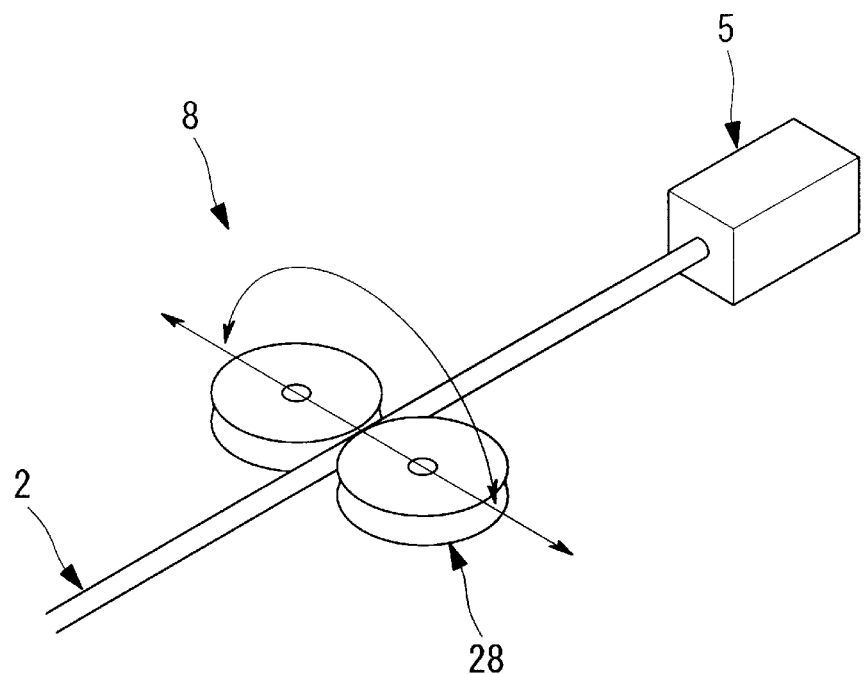
FIG. 10 is a schematic diagram illustrating an alternate example of FIG. 4.

Therefore, the total curvature length determined by applying the sign of the curvature direction and adding is detected for each curvature direction, and therefore the total curvature length for each curvature direction is analyzed for the portion of the curvature direction caused by the pulley sets 26, 27, and the path length difference caused by three-dimensional curvature is eliminated by determining the amount of travel of the pulley sets 26, 27 for adjusting the curvature lengths. As one of the ordinary skill in the art would appreciate three or more pulley sets 26, 27 may be used for the operation described hereinbefore. Furthermore, as illustrated in FIG. 10, it is also possible to provide a single pulley set (curvature length adjusting portion) 28, and to make the movement direction of the slider (not illustrated in the drawings) that supports the pulley set 28 able to be rotated around the longitudinal axis of the insertion portion 2 that extends straight from the driving portion 5.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A flexible manipulator, comprising:
    an elongated portion having two or more paths configured to pass through in the longitudinal direction thereof;
    a movable portion located on a distal end of the elongated portion;
    a driving portion located on a proximal end of the elongated portion, the driving portion is configured to generate a power for moving the movable portion;
    two or more wires configured to transmit a power from the driving portion to the movable portion, the two or more wires are configured to pass through into each of the two or more paths;
    a measuring portion configured to measure a curvature length of the elongated portion; and
    an adjusting portion configured to cause bending in the vicinity of a base end of the elongated portion so as to adjust the curvature length of the elongated portion as a predetermined length.

2. The flexible manipulator according to claim 1, wherein the two or more paths are formed in a spiral shape around the center axis; and
    the predetermined length is an integer multiple of the path pitch.

3. The flexible manipulator according to claim 1, wherein the predetermined length is a length that minimizes the difference to the curvature length of the elongated portion measured by the measuring portion.

4. The flexible manipulator according to claim 1, wherein the adjusting portion comprising:
    a pressing portion configured to be contacted by the elongated portion from the outside in the radial direction in the vicinity of the base end of the elongated portion, and
    a pressing portion driving mechanism configured to cause the pressing portion to move in the radial direction of the elongated portion.

5. The flexible manipulator according to claim 4, wherein the pressing portion comprises a cylindrical outer peripheral surface with a predetermined radius configured such that the elongated portion extends along the circumferential direction.

6. The flexible manipulator according to claim 5, wherein the pressing portion comprises a pulley.

7. The flexible manipulator according to claim 1 further comprising:
    a linear moving mechanism configured to cause the driving portion to move in the direction of the longitudinal axis of the elongated portion, synchronous to the movement of the pressing portion by the pressing portion driving mechanism.

8. The flexible manipulator according to claim 1, wherein the elongated portion is defined as a long narrow flexible tube having two or more paths that pass through in a longitudinal direction on an outside in a radial direction with respect to a center axis thereof.

9. The flexible manipulator according to claim 8, wherein the elongated portion includes two or more long narrow power transmission portions configured to pass through the respective two or more paths thereof so as to transmit the power from the driving portion to the movable portion.

10. The flexible manipulator according to claim 8, wherein the flexible manipulator is constructed so as to suppress the occurrence of path length difference of a plurality of power transmission portions with respect to various curvature lengths of the elongated portion and to prevent a loss of control of the movable portion by reducing the friction applied to the plurality of power transmission portions.

11. A flexible manipulator comprising:
an elongated portion;
a movable portion being attached on a tip end of the elongated portion;
a driving portion being attached on a base end of the elongated portion to transmit power thereto;
a curvature length measuring portion configured to measure a curvature length of the elongated portion; and
a curvature length adjusting portion configured to cause bending in the vicinity of the base end of the elongated portion so as to adjust the curvature length of the elongated portion as a predetermined length.

12. The flexible manipulator according to claim 11, wherein the elongated portion is defined as a long narrow flexible tube having two or more paths that pass through in a longitudinal direction on an outside in a radial direction with respect to a center axis thereof.

13. The flexible manipulator according to claim 12, wherein the elongated portion includes two or more long narrow power transmission portions configured to pass through the respective two or more paths thereof so as to transmit the power from the driving portion to the movable portion.

* * * * *